United States Patent
Heuer

(10) Patent No.: US 10,881,435 B2
(45) Date of Patent: Jan. 5, 2021

(54) POLYAXIAL PEDICLE SCREW

(71) Applicant: SILONY MEDICAL INTERNATIONAL AG, Frauenfeld (CH)

(72) Inventor: Frank Heuer, Filderstadt (DE)

(73) Assignee: Silony Medical International AG, Frauenfeld (CH)

(*) Notice: Subject to any disclaimer, the term of this patent is extended or adjusted under 35 U.S.C. 154(b) by 142 days.

(21) Appl. No.: 16/311,229

(22) PCT Filed: Jun. 28, 2017

(86) PCT No.: PCT/EP2017/066011
§ 371 (c)(1),
(2) Date: Dec. 19, 2018

(87) PCT Pub. No.: WO2018/024414
PCT Pub. Date: Feb. 8, 2018

(65) Prior Publication Data
US 2019/0274738 A1 Sep. 12, 2019

(30) Foreign Application Priority Data

Aug. 2, 2016 (DE) .................. 10 2016 114 266

(51) Int. Cl.
*A61B 17/70* (2006.01)
*A61B 17/86* (2006.01)
*A61B 90/00* (2016.01)

(52) U.S. Cl.
CPC ...... *A61B 17/7037* (2013.01); *A61B 17/7032* (2013.01); *A61B 17/7076* (2013.01);
(Continued)

(58) Field of Classification Search
CPC .. A61B 17/7001; A61B 17/7032–7046; A61B 17/8605–866
See application file for complete search history.

(56) References Cited

U.S. PATENT DOCUMENTS 10,117,680 B2 * 11/2018 Trautwein .......... A61B 17/7032
10,251,677 B2 * 4/2019 Heuer ................ A61B 17/7037
(Continued)

FOREIGN PATENT DOCUMENTS

| EP | 2502594 A1 | 9/2012 |
| EP | 2638874 A2 | 9/2013 |
| WO | 2015155702 A1 | 10/2015 |

OTHER PUBLICATIONS

International Search Report and Written Opinion from PCT/EP2017/066011 dated Sep. 18, 2017.
German Examination Report dated Mar. 8, 2017.

*Primary Examiner* — Tessa M Matthews
(74) *Attorney, Agent, or Firm* — Dilworth & Barrese, LLP

(57) ABSTRACT

The invention relates to a polyaxial pedicle screw (2) comprising a screw anchor (4), which has a threaded shaft (6) and a head (8), and comprising a fork head (10), which is U-shaped in side view and has a receiving opening (16) for a corrective element, in particular a correcting rod, and two arms (12), wherein the head is polyaxially pivotably mounted in a distal end region (14) of the fork head and the fork head can be fixed in a pivoted position intended by the surgeon relative to the head, and also comprising a pressure piece (18) which can be arranged in the fork between the head and the corrective element which, on the one hand, rests on the head and, on the other hand, can be loaded by the corrective element, wherein the region of one arm of the fork head the pressure piece is supported by means of a pivot bearing (54) against this arm in the axial direction (20), and that diametrically opposite the pressure piece has a receiving region (42) for a positioning force (44) acting in the axial direction, which attempts to the pivot the pressure piece in the distal direction relative to the (Continued)

Figure 1:
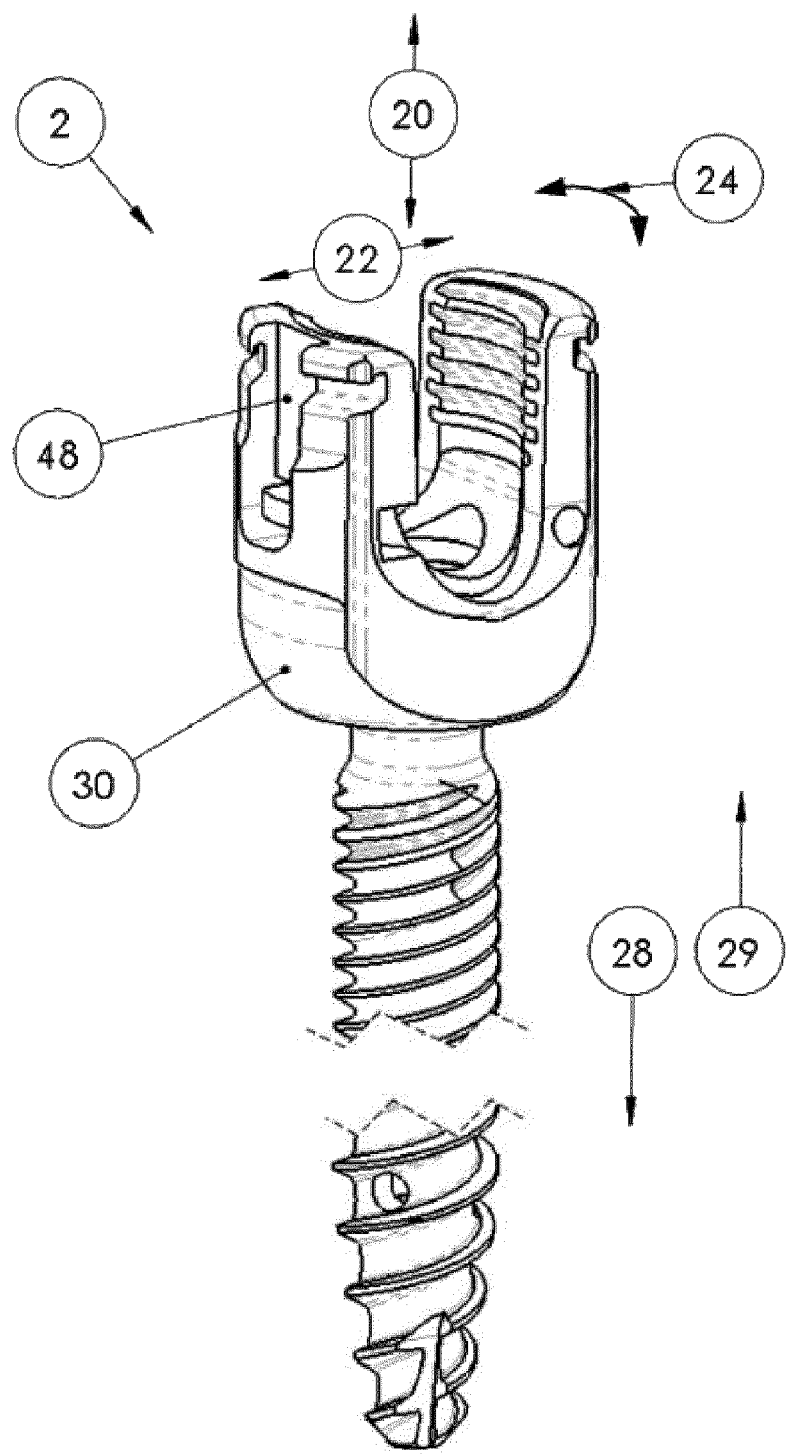

pivot bearing and in this way exerts the temporarily acting force in the direction of the head (8).

19 Claims, 9 Drawing Sheets

(52) U.S. Cl.
CPC ........ *A61B 17/7082* (2013.01); *A61B 17/863* (2013.01); *A61B 17/864* (2013.01); *A61B 2090/037* (2016.02)

(56) References Cited

U.S. PATENT DOCUMENTS

| | | |
|---|---|---|
| 2010/0262196 A1 | 10/2010 | Barrus et al. |
| 2012/0245640 A1 | 9/2012 | Auerbach et al. |
| 2013/0018422 A1* | 1/2013 | Rinner ............... A61B 17/7049 606/278 |
| 2014/0236236 A1 | 8/2014 | Kruger |
| 2014/0236239 A1* | 8/2014 | Biedermann ...... A61B 17/7037 606/278 |
| 2017/0020576 A1 | 1/2017 | Siccardi et al. |
| 2019/0274738 A1* | 9/2019 | Heuer ................ A61B 17/7076 |

* cited by examiner

DETAIL Z

POLYAXIAL PEDICLE SCREW

This application claims priority to German Patent Application No. 10 2016 114 266.2 filed on Aug. 2, 2016.

The invention relates to a polyaxial pedicle screw comprising a screw anchor, which has a threaded shaft and a head, and comprising a fork head, which is U-shaped in side view and has a receiving opening for a corrective element, in particular a correcting rod, and two arms, wherein the head of the screw anchor is polyaxially pivotably mounted in a distal end region of the fork head and the fork head is fixed or can be fixed in the bone in a pivoted position desired by the surgeon relative to the head of the screw anchor, wherein the fork head has an axial direction and a direction radial to this, as well as a distal end adjacent to the screw anchor and has a proximal end facing away from this in the axial direction so that a distal and a proximal direction are also defined, wherein the arms extend in the proximal direction starting from a distal region of the fork head and delimit proximal free ends and the receiving opening between them for the corrective element, wherein the arms have a radially outer circumferential region, in which at least one retaining groove or some other instrument placement position is formed for engaging with the fork head via a handling instrument, and with a pressure piece that can be arranged between the head of the screw anchor and the corrective element and which, on the one hand, rests on the head of the screw anchor and, on the other hand, can be loaded by the corrective element, wherein a temporarily acting force can be exerted in the direction of the head of the screw anchor on the pressure piece via a handling instrument engaging on the fork head or via another instrument, so that the fork head is thereby temporarily fixed in a pivoted position desired by the surgeon relative to the head of the screw anchor, whereas the corrective element remains movable as long as the corrective element, the fork head, the pressure piece and the head of the screw anchor are permanently fixed in a desired position and orientation relative to each other.

A pedicle screw of this type is known in particular from EP 2 502 594 B1 or from US 2014/0236236 A1.

In these pedicle screws, the pressure piece is pressed toward the head of the screw anchor on diametrically opposed sides at two or at four points. The access space on the fork head needed for this is considerable.

In a further pedicle screw according to US 2010/0262196 A1, the pressure piece has a groove on its outer circumference extending in the axial direction for receiving a pin extending in the radial direction inward through the fork head. This arrangement creates a positive alignment of the pressure piece within the fork head.

The present invention is based on the object of creating a polyaxial pedicle screw of the aforementioned type, in which the access space to be kept open in the fork head is as small as possible and in which a high positioning force and thus a secure temporary fixing can be realized.

This object is achieved according to the invention by a polyaxial pedicle screw of the aforementioned type in that the pressure piece in the region of an arm of the fork head is supported against this arm in the axial direction via a pivot bearing and in that the pressure piece has a receiving region diametrically opposite for a positioning force acting in the axial direction so as to pivot the pressure piece in the distal direction relative to the pivot bearing and thereby exerting the temporarily acting force in the direction of the head of the screw anchor.

Because the pressure piece provided according to the invention is minimally pivotable within the fork head, it is sufficient if the positioning force acting in the axial direction is introduced only at a single point in the pressure piece diametrically opposed to the pivot bearing. Therefore, in contrast to the previously known pedicle screws, there needs to be engagement only via a single actuator—in particular in the form of a push rod, a push plunger or a push punch or the like—at a single point of the pressure piece. The required access space for the actuator is reduced with respect to the prior art. A further essential advantage can be seen in that the pressure piece functions to a certain degree as a clamping lever. The positioning force acting in the axial direction on the receiving region of the pressure piece is therefore increased, somewhat similar to a nutcracker having two clamping arms.

According to an advantageous and easily realizable embodiment of the invention, the pivot bearing has a longitudinal shaft element inserted into the fork head that extends in a plane orthogonal to the axial direction of the fork head and against which the pressure piece is supported in the axial direction. The shaft element can be formed by a pin that can be inserted into the receiving opening of the fork head from outside.

In an operational state, the longitudinal shaft element is preferably approximately parallel to the corrective element inserted into the fork head. It has proven to be advantageous if the longitudinal shaft element is incorporated at its ends into the wall of the fork head and projects with a central section into the interior space delimited by the arms of the fork head, meaning inward.

It can also prove to be advantageous if the pivot bearing comprises a support formed radially to the inside on the fork head against which the pressure piece is supported in the axial direction. This support can, to some extent, be formed at a point, or it can have an extension transverse to the pivot plane of 0.5-5 mm, specifically 0.5-3 mm.

It can also prove to be advantageous if this support is formed by a free end of a pin that is inserted from the outside radially inward through an arm of the fork head.

According to another embodiment, it can prove to be advantageous if the support is formed by a step or groove flank on the fork head, specifically formed as one piece with the fork head. In such a case, the support can be created during the shaping of the fork head without an additional part being necessary.

It has proven to be advantageous if the pivot bearing comprises a recess in the pressure piece for forming the pivot bearing between the pressure piece and the fork head. A shaft element or some other support, in particular in the form of a pin or an end of a pin, can engage into this recess to form the pivot bearing point.

It may prove to be advantageous if the pivot bearing comprises a radially projecting support section on the pressure piece, by means of which the pressure piece is axially supported on the fork head and is thereby pivotable.

It would be conceivable that the receiving region of the pressure piece is formed for the positioning force acting in the axial direction from a distal end of the pressure piece without the regular form of the pressure piece being changed to configure the receiving region. In comparison, it has proven to be advantageous if the receiving region for the positioning force acting in the axial direction of the pressure piece is formed from a radial projection or extension of the pressure piece. Through this measure, the receiving region of the pressure piece can be displaced farther radially outward, which further strengthens the force acting on the head of the screw anchor via the lever action. The aforementioned projection or extension can be formed as one piece with the pressure piece, or it can be added as a separate element on the pressure piece.

In particular, if the receiving region is formed by a radial projection or extension of the pressure piece, it proves to be advantageous if the fork head has a recess for the receiving region of the pressure piece. The receiving region of the pressure piece can extend radially outward through this recess.

This recess for the receiving region of the pressure piece can be extended in the axial direction or in the circumferential direction on an arm of the fork head, in each case to the inside and in each case opening inwardly. For example, the recess could extend in an axial direction through an internal thread section of the arm so that the pressure piece can be inserted into the fork head from above, wherein the extension projects radially inward into the recess. However, it can also prove advantageous if the recess extends in the circumferential direction or transverse to the axial direction beginning from a lateral flank of the arm. In such a case, the projection or extension of the pressure piece can be screwed into this recess.

It further proves advantageous, if the recess is formed and extends in the radial direction through a wall region of an arm of the fork head. Thus, the projection or extension of the pressure piece passes through the recess radially outward so that its receiving region for the positioning force is exposed radially outwardly.

Advantageously, the recess of the fork head is formed and extends beginning from a flank of the arm on the inside of the arm first inwardly in the circumferential direction or transverse to the axial direction and then in the radial direction through a wall region of the arm. In this way, an operator-friendly mounting of the pressure piece on the fork head is possible in that the base piece is inserted in the axial direction and then rotated around the axial direction until the receiving region of the pressure piece engages into the radial recess or engages through it. Specifically, it is conceivable and advantageous if the recess extends in the radial direction completely through an arm of the fork head, meaning opens out into the outer periphery of the arm.

The access recess in the fork head mentioned at the outset for the handling instrument or for another instrument for exerting the positioning force acting in the axial direction on the receiving region of the pressure piece can be formed in different ways on or in an arm of the fork head. It proves to be advantageous if the fork head has an access recess in precisely one of the arms through which the receiving region of the pressure piece can be accessed via the handling instrument or the other instrument.

It proves to be expedient if the access recess extends in the axial direction beginning at a proximal end of the arm of the fork head because the axial direction represents the typical direction for access to the pedicle screw.

In a further development of the inventive concept, it is conceivable and advantageous if the access recess is formed radially to the inside and is open radially inwardly or is formed radially to the outside and is open radially outwardly, or is formed as an axial bore in the arm.

If the access recess is formed as an axial bore in the arm, the axial bore can have internal threads into which the other instrument can be screwed via a threaded plunger section, so that the threaded plunger section can be tightened with its distal end against the receiving section of the pressure piece.

In all embodiments, it proves advantageous if the pivot bearing has an axial clearance such that, upon introduction of force in the axial direction, the pressure piece can perform an axial adjustment movement via the corrective element without the adjustment movement being hindered by the pivot bearing. In this manner, tensile stresses or torsional stresses that could be caused by a hinged linkage of the pressure piece can be prevented from occurring inside the pressure piece during the final, permanent fixing of the components of the polyaxial pedicle screw. Because the regions of the pressure piece and of the fork head braced against one another that form the pivot bearing are provided with an axial play, a pivot bearing can be realized, on the one hand, for forming the temporary clamping force, and a certain axial adjustability can be realized, on the other hand, for the final, permanent fixing of the components.

Figure 2:
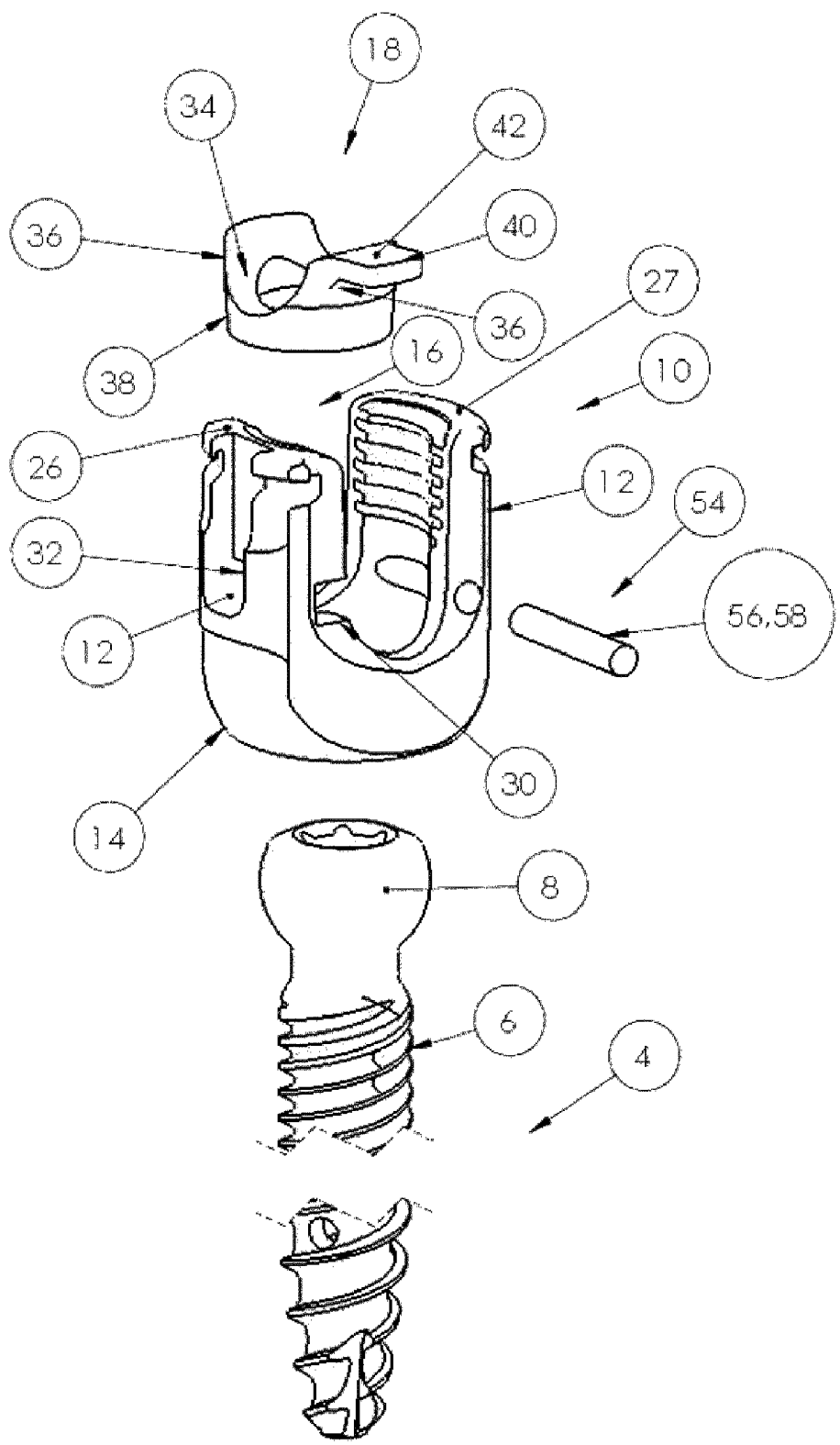
Figure 3:
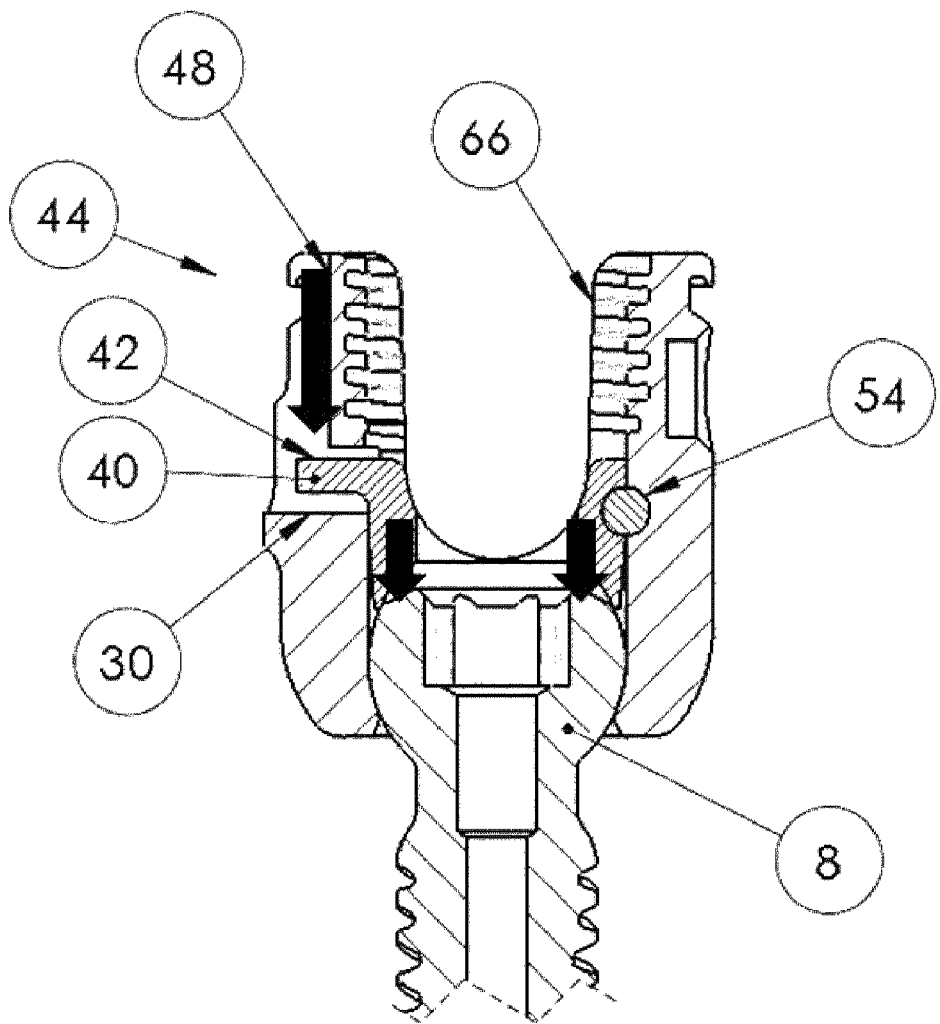
Figure 3:
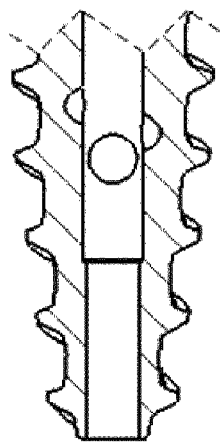
Figure 4:
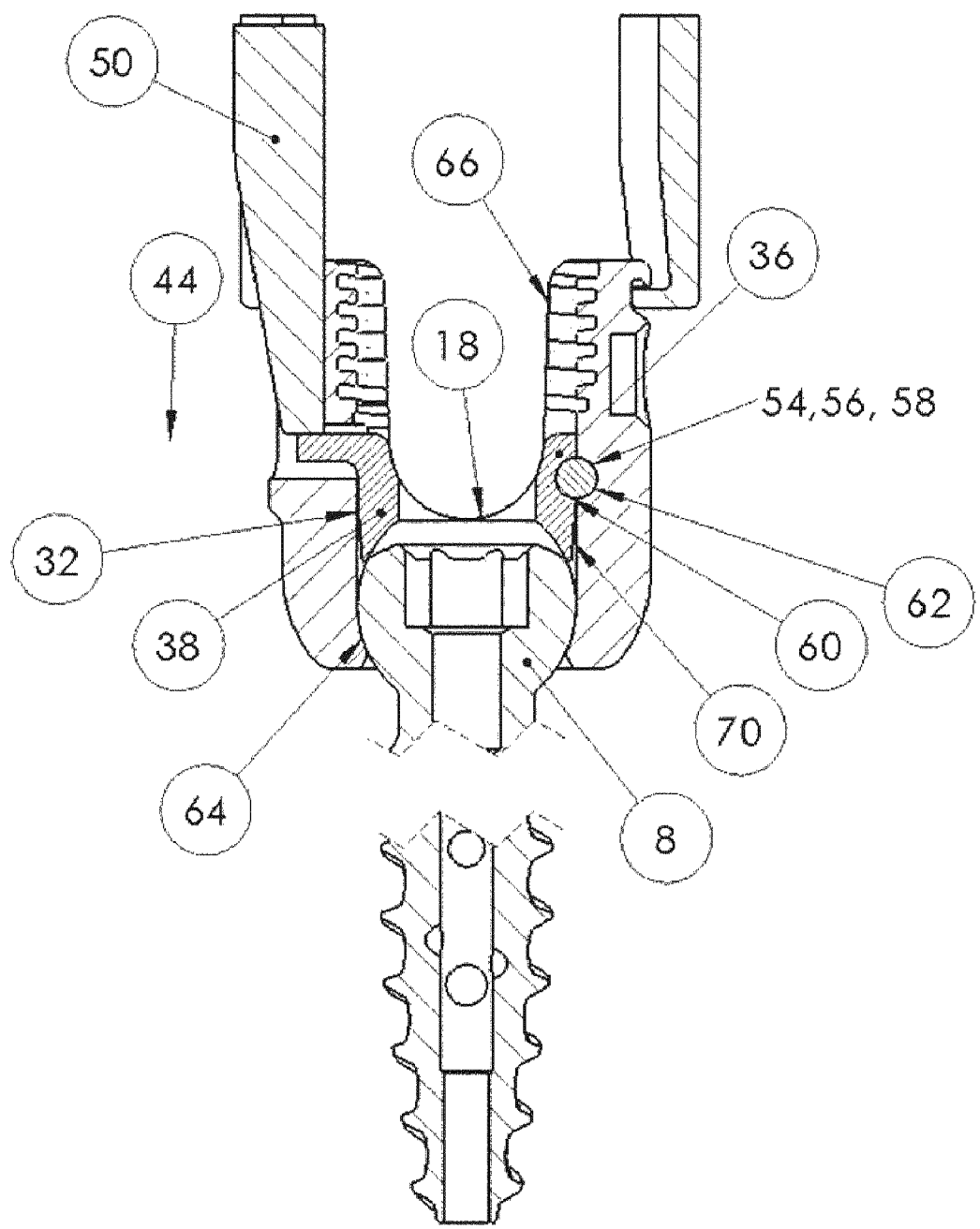
Figure 5:
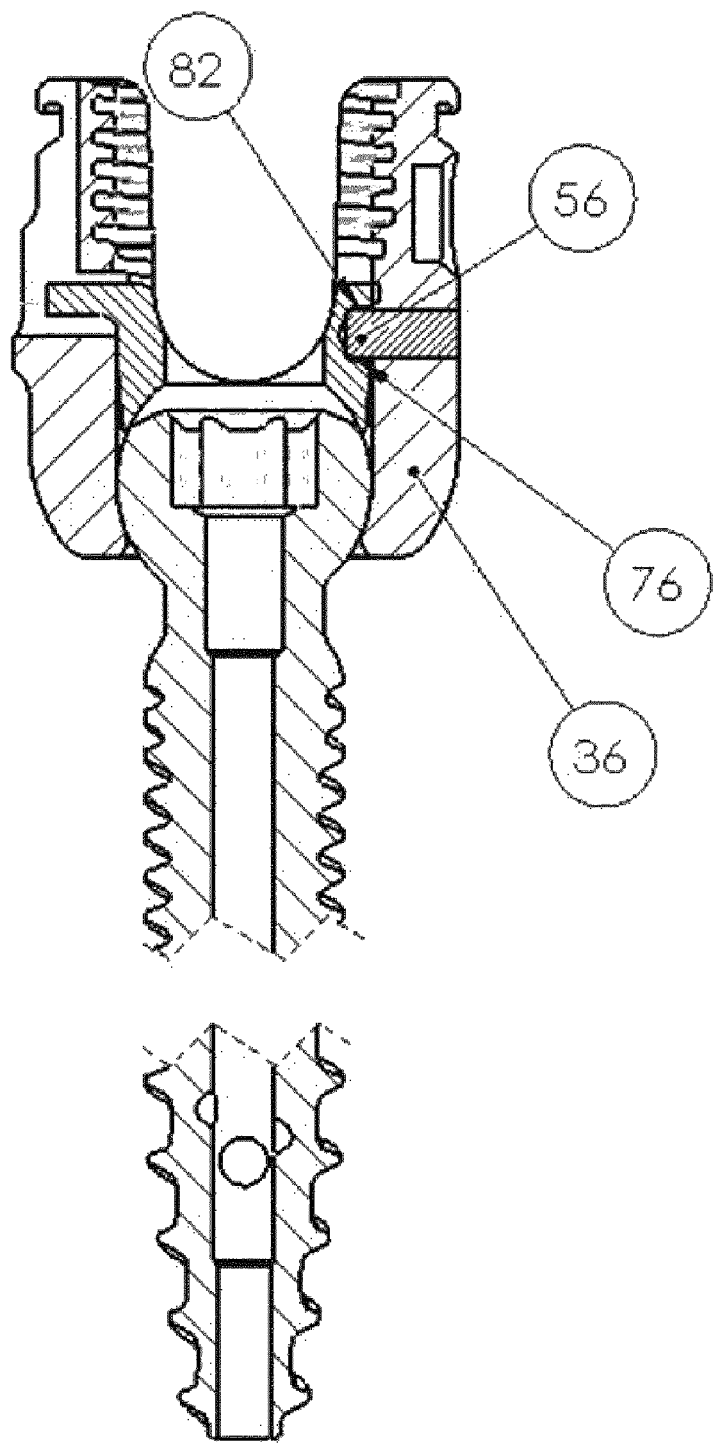
Figure 6:
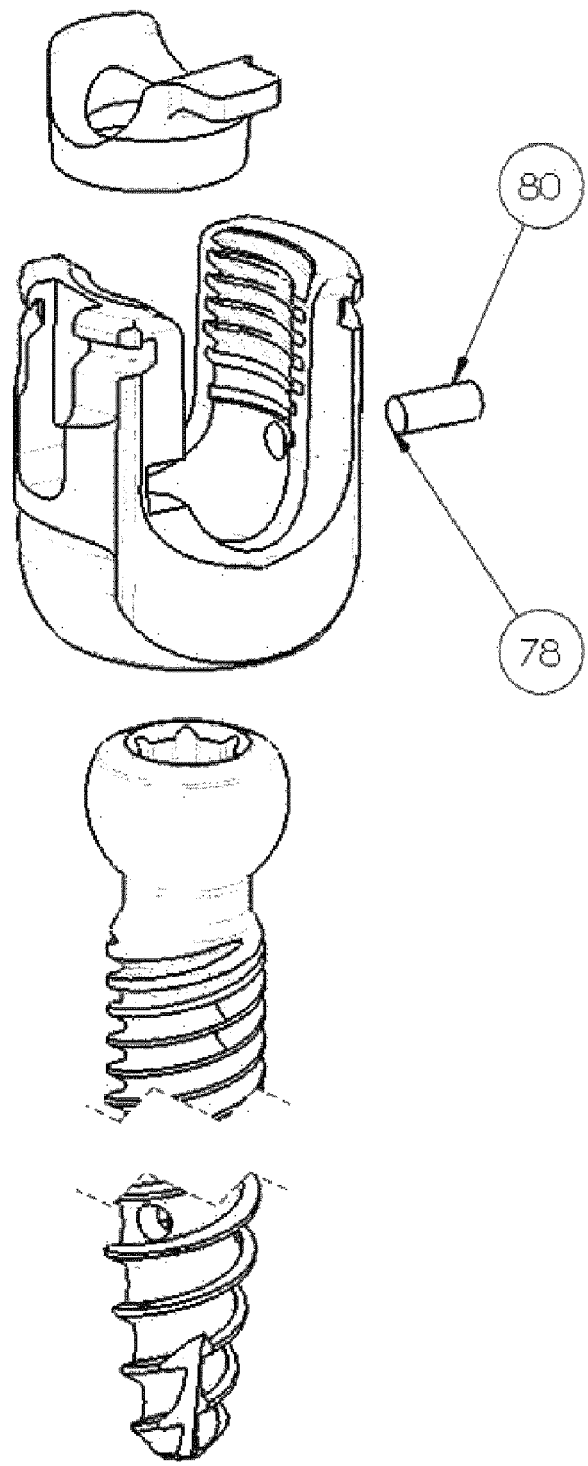
Figure 8:
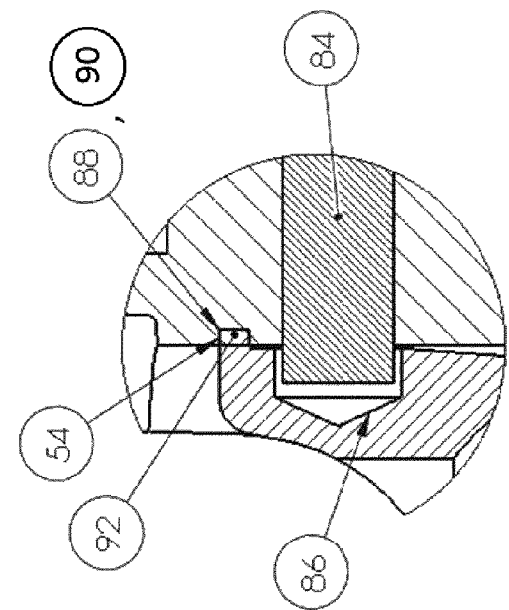
Figure 7:
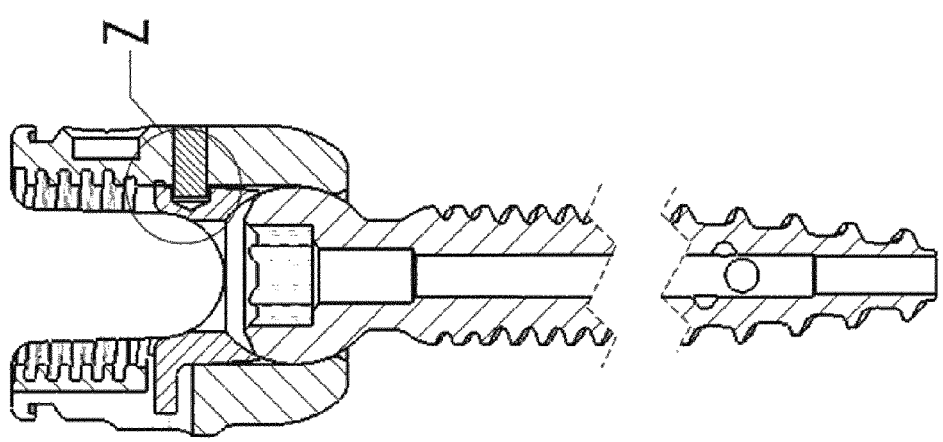
Figure 9:
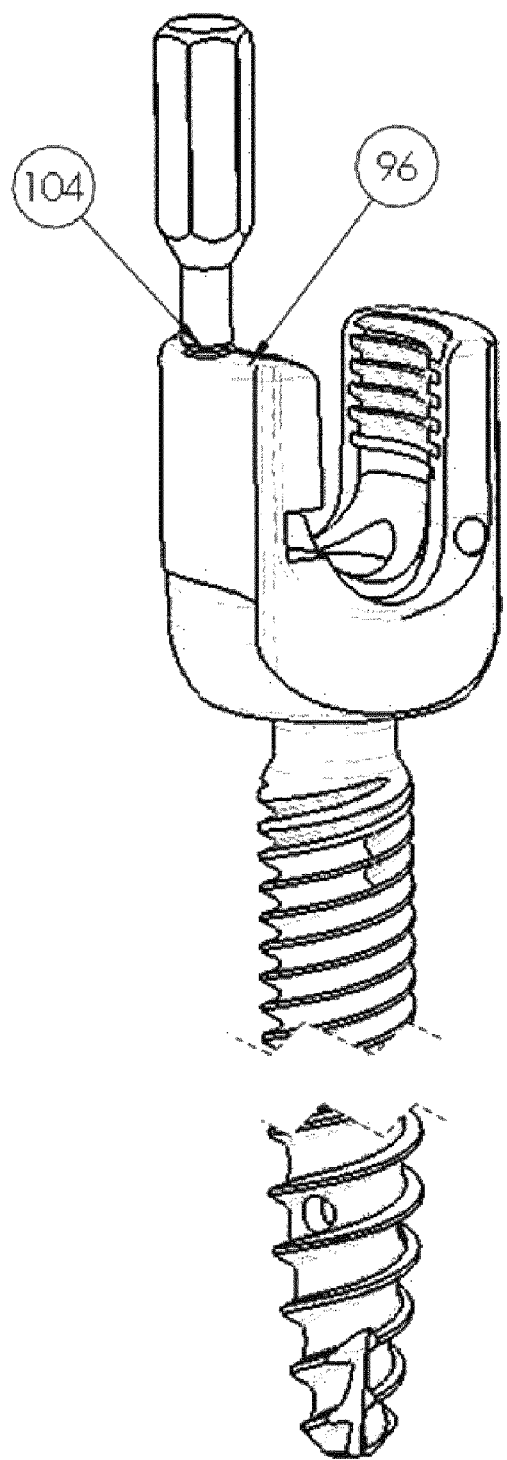
Figure 10:
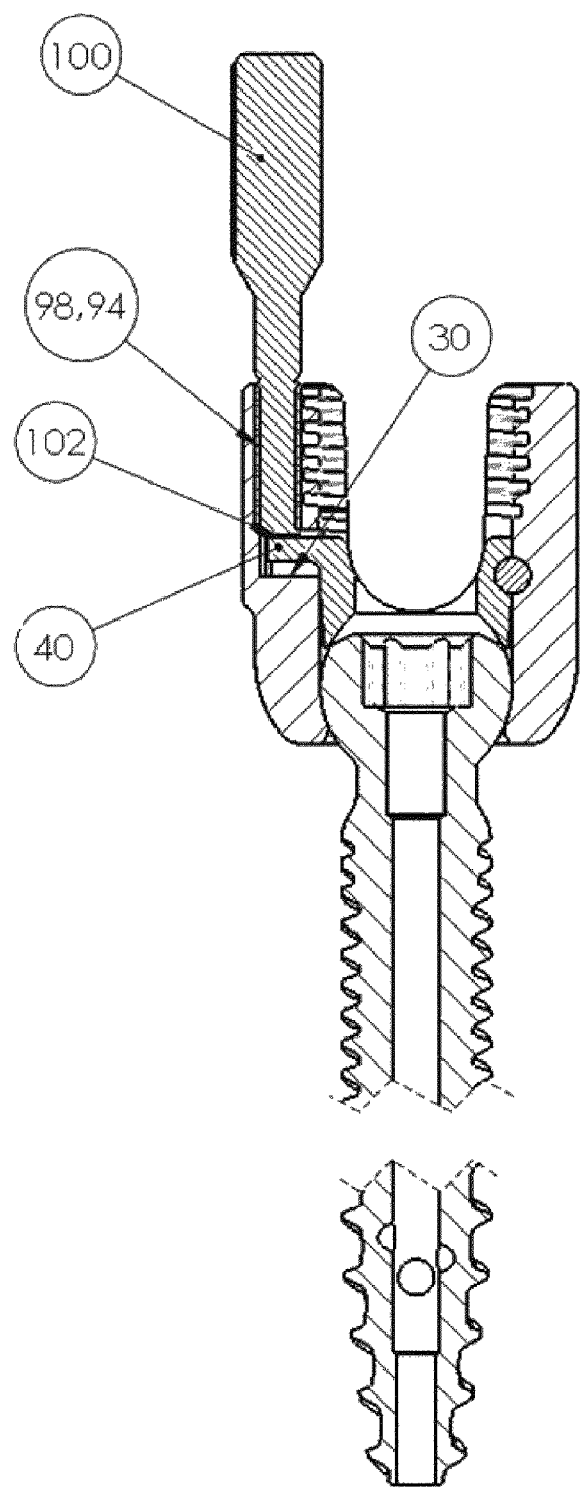

Additional features, advantages and details of the invention derive from the attached claims and from the detailed drawing and the following description of the embodiments according to the invention. Shown in the drawings are:

FIG. 1 a perspective view of an embodiment of a polyaxial pedicle screw according to the invention;

FIG. 2 a perspective view of the pedicle screw according to FIG. 1 shown in an exploded view;

FIG. 3 a sectional view of the pedicle screw according to FIG. 1 with the sectional plane including the axial direction;

FIG. 4 the sectional view according to FIG. 3 with a handling instrument engaging the pedicle screw and exerting a temporary clamping;

FIG. 5 a sectional view of a further embodiment of a polyaxial pedicle screw according to the invention;

FIG. 6 a perspective view of the components of the pedicle screw according to FIG. 5 shown in an exploded view;

FIG. 7 a sectional view of a further embodiment of a polyaxial pedicle screw according to the invention;

FIG. 8 a detail of FIG. 8;

FIG. 9 a perspective view of a further embodiment of a polyaxial pedicle screw according to the invention;

FIG. 10 a sectional view of the pedicle screw according to FIG. 9 with the sectional planes including the axial direction.

FIGS. 1 to 4 show a polyaxial pedicle screw 2 according to the invention. Pedicle screw 2 comprises a screw anchor 4 with threaded shaft 6 and head 8, as well as a fork head 10 with two arms 12 that, beginning at a distal end region 14 of fork head 10, extend in the proximal direction thus, away from the screw anchor 4 and terminate exposed. They delimit a U-shaped receiving opening 16 for a pressure piece 18 and a corrective element not shown, specifically a corrective rod that is inserted into receiving opening 16 and connects adjacent or, where applicable, a plurality of adjacent pedicle screws to each other. Head 8 of screw anchor 4 is polyaxially pivotably mounted in the distal end region 14 of fork head 10. When enough force is exerted on pressure piece 18 in the direction of head 8, fork head 10 can be placed so as to be non-adjustable relative to head 8 of the screw anchor as a result of the clamping action created thereby, which will be explained in detail below. Fork head 10 also defines an axial direction 20, a direction 22 radial thereto and a circumferential direction 24, as well as the distal end region 14 and a proximal end region 26 or a proximal end 27. Thus, a distal direction 28 and a proximal direction 29 are also specified.

Precisely one arm 12 of fork head 10 has a recess 30 on its interior that extends beginning from a lateral flank of the arm in circumferential direction 24 or at least orthogonally to axial direction 20. This recess 30 further extends in radial direction 22 through a wall region 32 of arm 12 and opens into the outer periphery of arm 12.

As can be seen from the illustration of pressure piece 18 (best in FIG. 2), pressure piece 18 comprises a roughly half-shell shaped receiving means 34 for a rod-shaped corrective element. This half-shell shaped receiving means 34 is laterally delimited by wall sections 36 extending in the distal direction that are located opposite each other and extend in the distal direction beginning at an annular, closed base section 38 of pressure piece 18. A projection or extension 40 that begins at one of the wall sections 36 extends outward in the radial direction. This projection or extension 40 is formed as a flap or a tongue that in the example case shown extends in a plane orthogonal to axial direction 20. Based on the orientation of pressure piece 18 shown in FIG. 2, pressure piece 18 can be inserted into fork head 10 in axial direction 20 and then rotated around axial direction 20 so that projection or extension 40 can engage into aforementioned recess 30 extending in the circumferential direction. In the orientation shown in FIGS. 1 and 3, projection or extension 40 projects through recess 30 that subsequently opens radially outward so that a free end of projection or extension 40 is exposed in the axial direction and forms a receiving area 42 for a positioning force acting in the axial direction, which is indicated in FIG. 3 with an arrow 44.

It can also be seen that the relevant arm 12 of fork head 10 has an access recess 48 on its exterior that in the example case shown is radially outwardly open and extends in axial direction 20, thereby allowing access to radially outwardly opening recess 30, in which receiving region 42 of the projection or extension 40 of pressure piece 18 comes to rest. In this way, a positioning force can be exerted on receiving region 42 of pressure piece 18 in the direction of arrow 44 in FIG. 3 through this access recess 48 by a plunger or punch of a handling instrument holding the pedicle screw of or another instrument. This is illustrated in FIG. 4. On its side diametrically opposite projection or extension 40, pressure piece 18 is designed so that it forms a pivot bearing 54 with the other arm 12 of fork head 10 and in such a way that pressure piece 18, upon the introduction of a positioning force in the direction of arrow 44, can be pivoted in a plane including axial direction 20 toward head 8 of screw anchor 4. In the exemplary embodiment of FIGS. 1 to 4, this is realized in that a shaft element 56, for example in the form of a cylindrical pin 58, is provided on the interior of arm 12 of fork head 10 to form the pivot bearing 54 in such a manner that it projects radially inward so that the pressure piece can pivotably support itself on it via a corresponding shaping of its wall section 36. For this purpose, wall section 36 in the example case shown has a corresponding recess 60 complementary to cylindrical pin 58, as can be best seen in FIG. 4. Cylindrical pin 58 is inserted, specifically press fitted, into a transverse bore 59 of arm 12.

Based on the configuration shown in FIG. 4, if a positioning force is now exerted in axial direction 44 on receiving region 42 of projection or extension 40 of pressure piece 18 via a plunger 50, then pressure piece 18 forms a lever that forms a pivot point 62 on pivot bearing 54. Because pressure piece 18 rests with its annular base section 38 upon head 8 of screw anchor 4, it therefore supports itself on the lower side of shaft element 56, meaning on the side facing head 8. It presses its annular base section 38 against head 8 of the screw anchor. As a result, head 8 of the screw anchor is pressed against a dome-like bearing or clamping surface 64 in the distal end region 14 of the fork head and can, as a result, be set temporarily fixed in place, meaning temporarily non-displaceably, as long as the positioning force is exerted upon pressure piece 18. During this, the surgeon has time to position the corrective element not shown in the figures inside the fork head and to carry out positioning and orientation changes of the vertebra, into which screw anchor 4 is screwed. Finally, all components can be thereby fixed in a desired orientation relative to each other by a set screw (not depicted) being screwed into internal threads 66 on arm 12 of fork head 10 that then presses on the corrective element, which in turn rests in the half-shell shaped receiving means 34 of pressure piece 18 and transmits this pressure to head 8 of the screw anchor. After fixing of this set screw, plunger 50 of the handling instrument can be released.

It can further be recognized from FIGS. 3 and 4 that a circumferential gap 70 is formed between fork head 10 and annular base section 38 of the pressure piece, which narrows in the proximal direction. In this manner, enough space is provided so that pressure piece 18 can pivot.

It has further proved advantageous if the design of pivot bearing 54 is such that the side of pressure piece 18 that faces shaft element 56 cooperates with play with shaft element 56 in the axial direction 20. It has already been noted that pressure piece 18 supports itself against shaft element 56 from below. It has therefore proven advantageous if recess 60, which surrounds shaft element 56, is larger in axial direction 20 than shaft element 56 in the area of recess 60. The result of this axial play is that pressure piece 18 can then shift symmetrically toward head 8 and brace against it without this resulting in twisting caused by the pivot bearing if the corrective element is pressed in the axial direction 20 onto the half-shell-shaped receiving means 34 during the final securing.

FIGS. 5 and 6 show a further exemplary embodiment, according to which pivot bearing 56 comprises a support 76 formed radially to the inside on fork head 10. This support 76 is formed by a free end 78 of a pin 80 inserted from outside radially inward through the relevant arm 12 of fork head 10. Corresponding wall section 36 of pressure piece 18 has a recess 82 for receiving free end 78 that opens radially outward and is dimensioned and formed with play relative to free end 78 of pin 80 in such a way that the pressure piece can pivot in a plane that includes axial direction 20, as is the case in the previously described embodiment.

An additional embodiment is illustrated in FIGS. 7 and 8. A pin 84 is also provided in this embodiment that engages into an opening 86 of pressure piece 18; it is, however, designed only as an anti-rotation device acting in the circumferential direction. Pivot bearing 54 in this case is realized by a groove flank 88 formed as one piece with the fork head that forms a support 90, wherein wall section 36 of the pressure piece has a support section 92 that forms a counter support extending radially outward, which engages into the groove and is supported axially against groove flank 88.

Finally, FIGS. 9 and 10 show an additional embodiment, according to which an access recess 94 is formed as an axial bore 98 beginning at a proximal end 96 of the corresponding arm 12. This axial bore 98 opens out into recess 30, through which extension 40 of pressure piece 18 extends. In the exemplary case, axial bore 98 has internal threads, into which a threaded plunger 100 can be screwed until it rests with its distal end 102 against extension 40 of the pressure piece and so as to pivot it toward head 8 of the screw anchor. It would also be conceivable for this threaded plunger 100 to comprise a predetermined breaking point 104 in the area of proximal end 96 of fork head 10, at which threaded plunger 100 can be sheared off.

The invention claimed is:

1. A polyaxial pedicle screw (2) comprising a screw anchor (4), which has a threaded shaft (6) and a head (8), and comprising a fork head (10), which is U-shaped in side view and has a receiving opening (16) for a corrective element, in particular a correcting rod, and two arms (12),
wherein the head (8) of the screw anchor (4) is polyaxially pivotably mounted in a distal end region (14) of the fork head (10) and the fork head (10) can be fixed in a pivoted position intended by a surgeon relative to the head (8) of the screw anchor (4) that is fixed or can be fixed in the bone,
wherein the fork head (10) has an axial direction (20) and a direction (22) radial to this as well as a distal end adjacent to the screw anchor (4) and has a proximal end (27) facing away from this in the axial direction (20), so that a distal direction (28) and a proximal direction (29) are defined as well,
wherein the arms (12) starting from the distal region of the fork head (10) extend in the proximal direction (29) and delimit proximal free ends for the corrective element and the receiving opening (16) between them,
wherein the arms (17) have a radially outer peripheral region, in which at least one retaining groove or other instrument placement location is formed in order to engage the fork head (10) via a handling instrument, and comprising a pressure piece (18) which can be arranged in the fork head (10) between the head (8) of the screw anchor (4) and the corrective element which, on the one hand, rests on the head (8) of the screw anchor (4) and, on the other hand, can be loaded by the corrective element,
wherein a force can be exerted temporarily on the pressure piece (18) in the direction of the head (8) of the screw anchor (4) via the handling instrument engaging on the fork head (10) or via another instrument so that the fork head (10) is temporarily fixed by this in a pivoted position intended by the surgeon relative to the head (8) of the screw anchor (4), whereas the corrective element remains movable as long as the corrective element, the fork head (10), the pressure piece (18) and the head (8) of the screw anchor (4) are durably fixed in a desired position and orientation with respect to one another via another adjusting means, characterized in that the pressure piece (18) in the region of an arm (12) of the fork head (10) is supported by means of a pivot bearing (54) against this arm (12) in the axial direction (20) and that diametrically opposite the pressure piece (18) has a receiving region (42) for a positioning force (44) acting in the axial direction (20) so as to pivot the pressure piece (18) in the distal direction relative to the pivot bearing (54) and thereby exerting the temporarily acting force in the direction of the head (8) of the screw anchor (4), and wherein the fork head (10) has an access recess (48) in precisely one of the arms (12), through which the receiving region of the pressure piece (18) can be accessed via the handling instrument or another instrument, and wherein the access recess (48) extends in the axial direction (20) beginning from a proximal end of the arm (12) of the fork head (10).

2. The pedicle screw of claim 1, wherein the pivot bearing (54) has an elongated shaft element (56) inserted into the fork head (10) that extends in a level orthogonal to the axial direction (20) of the fork head (10) and against which the pressure piece (18) is supported in the axial direction (20).

3. The pedicle screw of claim 2, wherein the elongated shaft element (56) is a pin (58).

4. The pedicle screw of claim 2, wherein the elongated shaft element (56) extends roughly parallel to the corrective element inserted into the fork head.

5. The pedicle screw of claim 1, wherein the pivot bearing (54) comprises a support (76, 90) formed radially to the inside on the fork head (10), against which the pressure piece (18) is supported in the axial direction (20) by a counter support.

6. The pedicle screw of claim 5, wherein the support (76) is formed by a free end (78) of a pin (80) inserted from the outside radially inward through an arm (12) of the fork head (10).

7. The pedicle screw of claim 5, wherein the support (90) is formed by a step or groove flank (88) on the fork head (10), in particular formed as one piece with the fork head (10).

8. The pedicle screw of claim 1, wherein the pivot bearing (54) comprises a recess (60, 82) in the pressure piece (18).

9. The pedicle screw of claim 1, wherein the pivot bearing (54) comprises a radially projecting support section (92) on the pressure piece (18), by means of which the pressure piece (18) is pivotably supported on the fork head (10).

10. The pedicle screw of claim 1, wherein the receiving region (42) of the pressure piece (18) for the positioning force (44) acting in the axial direction (20) is formed by a radial projection or extension (40) of the pressure piece (18).

11. The pedicle screw of claim 1, wherein the fork head (10) has a recess (30) for the receiving region (42) of the pressure piece (18).

12. The pedicle screw of claim 11, wherein the recess (30) is respectively extended radially inward on an arm (12) of the fork head (10) in the axial direction (20) or in a circumferential direction (24) or transverse to the axial direction (20) and is respectively formed opening inwardly.

13. The pedicle screw of claim 11, wherein the recess (30) is formed and extended in the radial direction (22) through a wall region of an arm (12) of the fork head (10).

14. The pedicle screw of claim 13, wherein the recess (30) of the fork head (10) is formed beginning from a flank of the arm (12) on the inside of the arm and extends first inward in the circumferential direction (24) or transverse to the axial direction (20) and then in the radial direction (22) through a wall region (32) of the arm.

15. The pedicle of claim 11, wherein the recess (30) extends completely through an arm (12) of the fork head (10) in the radial direction (22) and, thus, opens out in the outer circumferential surface.

16. The pedicle screw of claim 1, wherein the access recess (48) is formed radially to the inside and opens radially inwardly or is formed radially to the outside and is open radially outwardly or is formed as an axial bore (98) in the arm.

17. The pedicle screw of claim 16, wherein the axial bore (98) has internal threads, into which the other instrument with a threaded tappet section (100) can be screwed so that the threaded tappet section can be tightened with its distal end (102) against the receiving section (42) of the pressure piece (18).

18. The pedicle screw of claim 1, wherein the pivot bearing (54) has an axial play such that, upon introduction of force in the axial direction (20) via the corrective element, the pressure piece (18) can perform an axial adjustment movement without this adjustment movement being hindered by the pivot bearing (54).

19. A polyaxial pedicle screw (2) comprising a screw anchor (4), which has a threaded shaft (6) and a head (8), and comprising a fork head (10), which is U-shaped in side view and has a receiving opening (16) for a corrective element, in particular a correcting rod, and two arms (12),
- wherein the head (8) of the screw anchor (4) is polyaxially pivotably mounted in a distal end region (14) of the fork head (10) and the fork head (10) can be fixed in a pivoted position intended by a surgeon relative to the head (8) of the screw anchor (4) that is fixed or can be fixed in the bone,
- wherein the fork head (10) has an axial direction (20) and a direction (22) radial to this as well as a distal end adjacent to the screw anchor (4) and has a proximal end (27) facing away from this in the axial direction (20), so that a distal direction (28) and a proximal direction (29) are defined as well,
- wherein the arms (12) starting from a distal region of the fork head (10) extend in the proximal direction (29) and delimit proximal free ends for the corrective element and the receiving opening (16) between them,
- wherein the arms (17) have a radially outer peripheral region, in which at least one retaining groove or other instrument placement location is formed in order to engage the fork head (10) via a handling instrument, and comprising a pressure piece (18) which can be arranged in the fork head (10) between he head (8) of the screw anchor (4) and the corrective element which, on the one hand, rests on the head (8) of the screw anchor (4) and, on the other hand, can be loaded by the corrective element,
- wherein a force can be exerted temporarily on the pressure piece (18) in the direction of the head (8) of the screw anchor (4) via the handling instrument engaging on the fork head (10) or via another instrument so that the fork head (10) is temporarily fixed by this in a pivoted position intended by the surgeon relative to the head (8) of the screw anchor (4), whereas the corrective element remains movable as long as the corrective element, the fork head (10), the pressure piece (18) and the head (8) of the screw anchor (4) are durably fixed in a desired position and orientation with respect to one another via another adjusting means, characterized in that the pressure piece (18) in the region of an arm (12) of the fork head (10) is supported by means of a pivot bearing (54) against this arm (12) in the axial direction (20) and that diametrically opposite the pressure piece (18) has a receiving region (42) for a positioning force (44) acting in the axial direction (20) so as to pivot the pressure piece (18) in the distal direction relative to the pivot bearing (54) and thereby exerting the temporarily acting force in the direction of the head (8) of the screw anchor (4) and, wherein the pivot bearing (54) comprises a support (76, 90) formed radially to the inside on the fork head (10), against which the pressure piece (18) is supported in the axial direction (20) by a counter support, and wherein the support (76) is formed by a free end (78) of a pin (80) inserted from the outside radially inward through an arm (12) of the fork head (10).

* * * * *